United States Patent
Umbricht et al.

(10) Patent No.: US 7,132,001 B2
(45) Date of Patent: Nov. 7, 2006

(54) 3-AMINOPHENOL DERIVATIVES AND DYES THAT CONTAIN THESE COMPOUNDS WHILE SERVING TO DYE KERATIN FIBERS

(75) Inventors: Gisela Umbricht, Marly (CH); Franco Jose Rosato, Liebefeld (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 324 days.

(21) Appl. No.: 10/487,631

(22) PCT Filed: Jan. 8, 2003

(86) PCT No.: PCT/EP03/00098

§ 371 (c)(1),
(2), (4) Date: Feb. 24, 2004

(87) PCT Pub. No.: WO03/087084

PCT Pub. Date: Oct. 23, 2003

(65) Prior Publication Data

US 2004/0231064 A1 Nov. 25, 2004

(30) Foreign Application Priority Data

Apr. 18, 2002 (DE) ................. 102 17 271

(51) Int. Cl.
*A61K 7/13* (2006.01)
(52) U.S. Cl. ............ 8/405; 8/406; 8/410; 8/411; 8/412; 8/421; 8/423; 548/400; 549/415; 549/476; 549/478; 549/479; 549/480; 549/497
(58) Field of Classification Search .......... 8/405, 8/409, 411, 412, 410, 421, 423, 406; 548/400; 549/415, 476, 478, 479, 480, 497
See application file for complete search history.

(56) References Cited

U.S. PATENT DOCUMENTS

| | | | | |
|---|---|---|---|---|
| 6,592,631 B1 * | 7/2003 | Chassot et al. | ................ | 8/405 |
| 6,840,965 B1 * | 1/2005 | Chassot et al. | ................ | 8/405 |

FOREIGN PATENT DOCUMENTS

| | | |
|---|---|---|
| EP | 0 850 638 A1 | 7/1998 |
| EP | 1 153 917 A | 11/2001 |
| WO | 95 15144 | 6/1995 |
| WO | 01 85683 A | 11/2001 |
| WO | 02 062783 A | 8/2002 |

OTHER PUBLICATIONS

Chapter "Protective Groups", in Organic Synthesis, Chapter 3, Wiley Interscience, 1991, pp. 143-174.
Chapter "Protective Groups", in Organic Synthesis, Chapter 7, Wiley Interscience, 1991, pp. 494-653.

* cited by examiner

*Primary Examiner*—Eisa Elhilo
(74) *Attorney, Agent, or Firm*—Michael J. Striker

(57) ABSTRACT

The object of the present patent application are 3-aminophenol derivatives of formula (I) or the physiologically compatible, water-soluble salts thereof

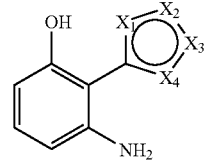

(I)

and colorants based on a developer-coupler combination containing these compounds.

13 Claims, No Drawings

3-AMINOPHENOL DERIVATIVES AND DYES THAT CONTAIN THESE COMPOUNDS WHILE SERVING TO DYE KERATIN FIBERS

BACKGROUND OF THE INVENTION

The present invention relates to novel 3-aminophenol derivatives substituted in the 2-position and to agents for dyeing keratin fibers, particularly human hair, containing these agents.

Oxidation dyes have attained substantial importance in the field of keratin fiber dyeing and particularly hair dyeing. The color is generated by reaction of certain developers with certain couplers in the presence of an appropriate oxidant. The developers used for this purpose are, in particular, 2,5-diaminotoluene, 2,5-diaminophenylethyl alcohol, p-aminophenols, 1,4-diaminobenzene and 4,5-diamino-1-(2-hydroxyethyl)pyrazole, whereas suitable couplers are, for example, resorcinol, 2-methylresorcinol, 1-naphthol, 5-amino-2-methylphenol, m-phenylenediamine, 2-amino-4-(2'-hydroxyethyl)amino-anisole, 1,3-diamino-4-(2'-hydroxyethoxy)benzene and 2,4-diamino-5-fluorotoluene.

In addition to being able to produce colors of the desired intensity, oxidation dyes used for dyeing human hair must meet many additional requirements. For example, such dyes must be unobjectionable from a toxicological and dermatological standpoint, and the hair colorations obtained must be highly resistant to light, permanent waving, acids and rubbing. In any case, however, in the absence of exposure to light, rubbing and chemical agents such colorations must remain stable for a period of at least 4 to 6 weeks. Moreover, it must be possible, by a combination of suitable developers and couplers, to produce a wide range of different color shades.

Although many couplers are already known, with the currently known colorants it is not possible to meet the requirements placed on a colorant in every respect. Hence, a need continues to exist for novel couplers that will meet the aforesaid requirements to an especially high degree.

SUMMARY OF THE INVENTION

We have now found that certain 3-aminophenol derivatives of general formula (I) meet the requirements placed on couplers to an especially high degree and with known developers give intense and unusually light-fast and wash-fast color shades.

Hence, the object of the present invention are novel 3-aminophenol derivatives of formula (I) or physiologically compatible, water-soluble salts thereof,

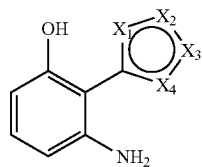
(I)

wherein
$X_1$, $X_2$, $X_3$ and $X_4$ independently of each other denote sulfur, nitrogen, N—R1, oxygen, C—R2, C—R3, C—R4 or C—R5, provided that at least one and at the most three of the $X_1$ to $X_4$ groups denote nitrogen, N—R1, sulfur or oxygen, and if several heteroatoms are present, at the most one of the $X_1$ to $X_4$ groups denotes sulfur, N—R1 or oxygen;

R1 denotes hydrogen, a $C_1$–$C_8$-alkyl group, a phenyl group, a ($C_2$–$C_4$)-hydroxyalkyl group or an acetyl group;

R2, R3, R4 and R5 independently of each other denote hydrogen, a halogen atom (F, Cl, Br, I), a cyano group, a $C_1$–$C_6$-alkyl group, a $C_1$–$C_4$-alkoxy group, a $C_1$–$C_4$-alkyl thioether group, a mercapto group, a nitro group, an amino group, a $C_1$–$C_4$-alkylamino group, a di($C_1$–$C_4$)-alkylamino group, a hydroxy-($C_2$–$C_4$)-alkylamino group, a di[hydroxy-($C_1$–$C_4$)-alkyl]amino group, a [dihydroxy-($C_3$–$C_4$)-alkyl]amino group, a trifluoromethyl group, an acetyl group, a trifluoroacetyl group, a formyl group, a trimethylsilyl group, a ($C_1$–$C_4$)-hydroxyalkyl group or a ($C_2$–$C_4$)-dihydroxyalkyl group, or two adjacent R2 to R5 groups together with the remainder of the molecule form a heterocyclic or carbocyclic, substituted or unsubstituted ring.

Suitable compounds of formula (I) are, for example: 3-amino-2-(3-thienyl)phenol, 3-amino-2-(3-furyl)phenol, 3-amino-2-(pyrrol-3-yl)phenol, 3-amino-2-(1-methyl-1H-pyrrol-3-yl)phenol, 3-amino-2-(1,3-thiazol-2-yl)phenol, 3-amino-2-(1,3-thiazol-5-yl)phenol, 3-amino-2-(2-thienyl)phenol, 3-amino-2-(2-furyl)phenol, 3-amino-2-(pyrrol-2-yl)phenol, 3-amino-2-(1-methyl-1H-pyrrol-2-yl)phenol, 3-amino-2-(2-chloro-3-(thienyl)phenol, 3-amino-2-(2-methyl-3-thienyl)phenol, 3-amino-2-(benzo[b]thiophen-2-yl)phenol, 3-amino-2-(5-phenyl-2-thienyl)phenol, 3-amino-2-(2-nitro-3-thienyl)phenol, 3-amino-2-(2-amino-3-thienyl)phenol, 3-amino-2-(2-acetyl-3-thienyl)phenol, 3-amino-2-(2-formyl-3-thienyl)phenol, 3-amino-2-(4-chloro-3-thienyl)phenol, 3-amino-2-(4-methyl-3-thienyl)phenol, 3-amino-(4-nitro-3-thienyl)phenol, 3-amino-2-(4-amino-3-thienyl)phenol, 3-amino-2-(4-acetyl-3-thienyl)phenol, 3-amino-2-(4-formyl-3-thienyl)phenol, 3-amino-2-(5-chloro-3-thienyl)phenol, 3-amino-2-(5-methyl-3-thienyl)phenol, 3-amino-2-(5-phenyl-3-thienyl)phenol, 3-amino-2-(5-nitro-3-thienyl)phenol, 3-amino-2-(5-acetyl-3-thienyl)phenol, 3-amino-2-(5-amino-3-thienyl)phenol, 3-amino-2-(5-formyl-3-thienyl)phenol, 3-amino-2-(benzo[b]thiophen-3-yl)phenol, 3-amino-2-(5-formyl-3-furyl)phenol, 3-amino-2-(3-chloro-2-thienyl)phenol, 3-amino-2-(3-methyl-2-thienyl)phenol, 3-amino-2-(3-nitro-2-thienyl)phenol, 3-amino-2-(3-amino-2-thienyl)phenol, 3-amino-2-(3-acetyl-2-thienyl)phenol, 3-amino-2-(3-formyl-2-thienyl)phenol, 3-amino-2-(4-chloro-2-thienyl)phenol, 3-amino-2-(4-methyl-2-thienyl)phenol, 3-amino-2-(4-nitro-2-thienyl)phenol, 3-amino-2-(4-amino-2-thienyl)phenol, 3-amino-2-(4-acetyl-2-thienyl)phenol, 3-amino-2-(4-formyl-2-thienyl)phenol, 3-amino-2-(5-chloro-2-thienyl)phenol, 3-amino-2-(5-methyl-2-thienyl)phenol, 3-amino-2-(5-nitro-2-thienyl)phenol, 3-amino-2-(5-amino-2-thienyl)phenol, 3-amino-2-(5-acetyl-2-thienyl)phenol, 3-amino-2-(5-formyl-2-thienyl)phenol, 3-amino-2-(5-formyl-2-furyl)phenol, 3-amino-2-(5-nitro-1,3-thiazol-2-yl)phenol, 3-amino-2-(5-amino-1,3-thiazol-2-yl)phenol, 3-amino-2-(2-nitro-1,3-thiazol-5-yl)phenol, 3-amino-2-(2-amino-1,3-thiazol-5-yl) phenol, 3-amino-2-(3,5-dimethyl-isoxazol-4-yl)phenol, 3-amino-2-(3,5-dimethyl-1H-pyrazol-4-yl)phenol and 3-amino-2-(5-nitro-4H-1,2,4-triazol-3-yl) phenol as well as the physiologically compatible, water-soluble salts thereof.

Preferred compounds of formula (I) are those wherein:
(i) $X_2$ denotes sulfur and $X_1$, $X_3$ and $X_4$ denote C—R2, C—R4 and C—R5 or (ii) $X_1$ denotes sulfur and $X_2$, $X_3$ and $X_4$ denote C—R3, C—R4 and C—R5.

Particularly preferred are the following compounds of formula (I):

3-amino-2-(3-thienyl)phenol, 3-amino-2-(2-thienyl)phenol, 3-amino-2-(benzo[b]thiophen-3-yl)phenol and 3-amino-2-(5-phenyl-2-thienyl)phenol as well as the physiologically compatible, water-soluble salts thereof.

The compounds of formula (I) can be used as the free bases as well as in the form of their physiologically compatible salts of inorganic or organic acids, for example hydrochloric acid, sulfuric acid, phosphoric acid, acetic acid, propionic acid, lactic acid or citric acid.

The 3-aminophenol derivatives of formula (I) of the invention can be prepared by methods of synthesis known from the literature, for example a) by tetrakis(triphenylphosphine)palladium(0)-catalyzed coupling of a halogen-substituted 3-aminophenol of formula (IIa) with a boric acid derivative of formula (IIIa) followed by removal of the protective group needed for the coupling reaction and by reduction of an optionally present nitro group;

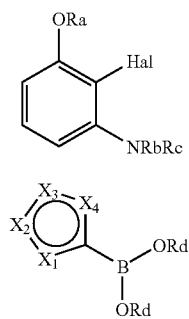

or b) by tetrakis(triphenylphosphine)palladium(0)-catalyzed coupling of an appropriate substituted 3-aminophenolboric acid derivative of formula (IIb)

with a halogen-substituted aromatic compound of formula (IIIb) followed by removal of the protective group needed for the coupling reaction and by reduction of an optionally present nitro group;

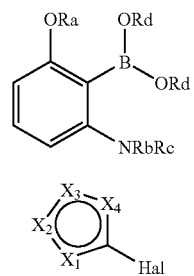

the other groups used in formulas (Ia), (IIb), (IIIa) and (IIIb) having the following meaning:

Ra denotes a protective group as described, for example, in the chapter on "Protective Groups" in Organic Synthesis, chapter 3, Wiley Interscience, 1991;

Rb and Rc independently of each other denote hydrogen or a protective group as described, for example, in the chapter on "Protective Groups" in Organic Synthesis, chapter 7, Wiley Interscience, 1991, or Rb and Rc together with the N-atom form a nitro group;

Rd denotes hydrogen or the two Rd groups together with the —O—B—O— group form an unsubstituted or substituted five-membered or six-membered cycloaliphatic ring;

Hal denotes F, Cl, Br or I; and $X_1, X_2, X_3$ and $X_4$ have the same meaning as in formula (I).

The 3-aminophenol derivatives of formula (I) are readily water-soluble and give colorations of excellent color intensity and color stability, particularly in terms of light fastness, wash fastness and rubbing fastness. Moreover, they have excellent storage stability particularly as constituents of the oxidative colorants described in the following.

Another object of the present invention is therefore an agent for coloring keratin fibers, for example wool, furs, feathers or hair and particularly human hair, said agent being based on a developer-coupler combination and being characterized in that it contains at least one 3-aminophenol derivative of formula (I) or a physiologically compatible, water-soluble salt thereof.

The 3-aminophenol derivatives of formula (I) are present in the colorant of the invention in a total amount from about 0.005 to 20 weight percent, an amount from about 0.01 to 5 weight percent and particularly from 0.1 to 2.5 weight percent being preferred.

Preferred developers are 1,4-diaminobenzene (p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(2-thienyl)benzene, 1,4-diamino-2-(3-thienyl)benzene, 1,4-diamino-2-(pyridin-3-yl) benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy) benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino] aniline, 4-[di(2-hydroxyethyl)amino]-2-methylaniline, 4-[(2-methoxyethyl)amino]aniline, 4-[(3-hydroxypropyl) amino]aniline, 4-[(2,3-dihydroxypropyl)amino]aniline, 1,4-diamino-2-(1-hydroxyethyl)benzene, 1,4-diamino-2-(2-hydroxyethyl)benzene, 1,4-diamino-2-(1-methylethyl) benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetra-aminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

Moreover, besides the compounds of formula (I) the colorant of the invention can also contain other known couplers, for example N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be contained in the colorant of the invention either individually or in admixture with each other, the total amount of couplers and developers in the colorant of the invention (based on the total amount of colorant) being from about 0.005 to 20 weight percent, preferably from about 0.01 to 5 weight percent and particularly from 0.1 to 2.5 weight percent, each.

The total amount of the developer-coupler combination contained in the colorant described herein is preferably from about 0.01 to 20 weight percent, an amount from about 0.02 to 10 weight percent and particularly from 0.2 to 6 weight percent being especially preferred. In general, the developers and couplers are used in approximately equimolar amounts. However, it is not disadvantageous if the developers are present in a certain excess or deficiency with respect to such an amount.

Moreover, the colorant of the invention can also contain other dye components, for example 6-amino-2-methylphenol and 2-amino-5-methylphenol as well as common synthetic or natural direct dyes, for example vegetable dyes or synthetic direct dyes from the group of acid or basic dyes (for example the cationic dyes described in WO 95/15144 or European Unexamined Patent Application EP 0 850 638), triphenylmethane dyes, aromatic nitro dyes, azo dyes and disperse dyes. The colorants of the invention can contain these dye components in an amount from about 0.1 to 4 weight percent.

Naturally, the additional couplers and the developers and other dye components, provided they are bases, can also be used in the form of their physiologically compatible salts of organic or inorganic acids, for example hydrochloric acid or sulfuric acid, or—if they contain aromatic OH— groups—in the form of salts of bases, for example as alkali metal phenoxides.

Moreover, if the colorants are used for dyeing hair, they can also contain common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be formulated, for example, as a solution, particularly an aqueous or aqueous-alcoholic solution. A particularly preferred formulation, however, is a cream, gel or emulsion. Such a preparation consists of a mixture of dye components and additives commonly used for such preparations.

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6.5 to 11.5, the adjustment to a basic value preferably being achieved with ammonia. However, amino acids and/or organic amines, for example monoethanolamine or triethanolamine, or inorganic bases, for example sodium hydroxide or potassium hydroxide can also be used. For pH adjustment in the acidic range, an inorganic or organic acid, for example phosphoric acid, acetic acid, citric acid or tartaric acid, can be used.

For use in oxidative dyeing of hair, the afore-described colorant is mixed with an oxidant just before use and the resulting mixture is applied to the hair in an amount sufficient for the hair treatment, in general in an amount from about 60 to 200 grams, depending on the fullness of the hair.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. If a 6% hydrogen peroxide solution is used as oxidant, the weight ratio of hair colorant to oxidant is from 5:1 to 1:2 and preferably 1:1. Larger amounts of oxidant are used primarily at higher dye concentrations in the hair colorant or when more pronounced hair bleaching is wanted at the same time. The mixture is allowed to act on the hair at 15 to 50° C. for about 10 to 45 minutes, preferably for 30 minutes, after which the hair is rinsed with water and dried. Optionally, following this rinsing the hair is washed with a shampoo and optionally post-rinsed with a weak organic acid, for example citric acid or tartaric acid. The hair is then dried.

The colorant of the invention containing a 3-aminophenol derivative of formula (I) as coupler gives colorations of excellent color stability, particularly in terms of light fastness, wash fastness and rubbing fastness. As far as the coloring properties are concerned, depending on the kind and composition of the dye components, the colorant of the invention provides a wide range of different color shades ranging from blond to brown, purple, violet, blue and black. Said shades are characterized by high color intensity. Furthermore, the very good coloring properties of the colorant of the present patent application are, in particular, characterized by the fact that this colorant also makes it possible to dye gray, chemically not previously damaged hair with good covering power and without any problems.

The following examples are intended to illustrate the subject matter of the invention more closely without limiting its scope.

EXAMPLES

Examples 1 to 6

Synthesis of 3-Aminophenol Derivatives of General Formula (I)

A. Synthesis of 2-bromo-3-nitrophenol

A solution of 10.5 g (152 mmol) of sodium nitrite in 40 mL of water was added slowly and dropwise to a suspension of 23.1 g (150 mmol) of 2-amino-3-nitrophenol in 40 ml of a 48% hydrobromic acid solution and 12 mL of water at 0° C. The mixture was then allowed to agitate at 0° C. for 15 minutes. Subsequently, a suspension of 22.5 g of copper(I) bromide ($Cu_2Br_2$; 78.7 mmol) in 75 mL of a 48% hydrobromic acid solution was added dropwise, and the mixture was allowed to agitate at 0° C. for 15 minutes and then at 100° C. for 1 hour. The reaction mixture was then cooled to about 5° C. and filtered, and the filter cake was washed with a small amount of water. This filter cake was then taken up with ethyl acetate and filtered through silica gel. The solvent was then evaporated to dryness under vacuum.

This gave 32.2 g. (98% of the theoretical) of 2-bromo-3-nitrophenol. The crude product thus obtained was used in the next step without additional purification.

$^1$H-NMR (300 MHz, $CDCl_3$): δ=7.47 ppm (dd, J=1.5 Hz/7.8 Hz, 1H, CH); 7.37 ppm (t, J=8.1 Hz, 1H, CH); 7.26 ppm (dd, J=1.5 Hz/8.1 Hz, 1H, CH); 6.08 ppm (s, 1H, OH). EI-MS: 219/217 [$M^+$] (40); 161/159 [$M^+$—C—$NO_2$] (24)

B. Synthesis of 2-bromo-1-(methoxymethoxy)-3-nitrobenzene 15 g (69 mmol) of 2-bromo-3-nitrophenol from step A was dissolved in 150 mL of dry acetonitrile and to it was added portionwise at 0° C. 3.5 g (117 mmol) of an 80% sodium hydride suspension. A solution of 6.1 g (75 mmol) of chloromethoxymethane in 50 mL of dry acetonitrile was then added. At the end of the addition, the mixture was allowed to agitate overnight at room temperature. Ten mL of ethanol was added to decompose excess sodium hydride. The reaction mixture was then filtered, and the filtrate was evaporated to dryness in a rotary evaporator under vacuum. The crude product thus obtained was used in the next step without further purification.

This gave 14.6 g (81% of the theoretical) of 2-bromo-1-(methoxymethoxy)-3-nitrobenzene as a brown oil.

$^1$H-NMR (300 MHz. DMSO): δ=7.60–7.48 ppm (m, 3H, arom. —CH); 5.41 ppm (s, 2H, $CH_2$); 3.44 ppm (s, 3H, $CH_3$). MS (API-ES neg.): 218/216 [M–H]$^-$ (100).

C. Synthesis of 3-aminophenols of Formula (I)

0.26 g (1.0 mmol) of 2-bromo-1-(methoxymethoxy)-3-nitrobenzene from step B and 1.5 mmol of the corresponding boric acid derivative were dissolved in 5 mL of 1,2-dimethoxyethane under argon. Then, 0.18 g (0.15 mmol) of tetrakis(triphenyl-phosphine) palladium(O) complex and 0.8 mL of a 2N aqueous potassium carbonate solution were added, and the reaction mixture was heated to 100° C. At the end of the reaction, the reaction mixture was poured into 10 mL of ethyl acetate, the organic phase was extracted with 5 mL of water and the aqueous phase was back-extracted twice with ethyl acetate. The combined organic phases were then dried with magnesium sulfate, and the solvent was distilled off in a rotary evaporator. The residue was purified on silica gel using heptane/ethyl acetate.

The product thus obtained was dissolved in 5 mL of ethanol and hydrogenated with gaseous hydrogen in the presence of about 50 mg of palladium (10% on active charcoal) at room temperature and normal pressure. At the end of the reaction, the reaction product was filtered through Cellite® and then concentrated. The resulting residue was treated with 1 mL of a 2.9-molar ethanolic hydrochloric acid solution or with 4-molar hydrochloric acid in dioxane. The reaction mixture was allowed to agitate for about one hour at room temperature. At the end of the reaction, the precipitate was filtered off, washed with ethanol (or dioxane) and then dried. If no precipitation has occurred, the solvent can be evaporated in a rotary evaporator.

1. 3-Amino-2-(3-thienyl)phenol hydrochloride

Boric acid derivative used: 3-thiophenylboric acid
Yield: 0.165 g (74% of the theoretical) $^1$H-NMR (300 MHz, DMSO): δ=9.90 ppm (s, 1H, OH); 7.68–7.63 ppm (m, 2H, arom. H); 7.23–7.17 ppm (m, 2H, arom. H); 6.88 ppm (t, J=6.9 Hz, 2H, arom. H); 3.8–3.3 ppm (br, NH$_3^+$). MS (API-ES pos.): 192 [M+H]$^+$ (20).

2. 3-Amino-2-(benzo[b]thiophen-3-yl)phenol hydrochloride

Boric acid derivative used: 1-benzothiophen-3-ylboric acid

Yield: 0.050 g (18% of the theoretical) MS (API-ES pos.): 242 [M+H]$^+$(50).

3. 3-Amino-2-(2-thienyl)phenol hydrochloride

Boric acid derivative used: 2-thiophenylboric acid

Yield: 0.150 g (26% of the theoretical) $^1$H-NMR (300 MHz. DMSO): δ=10.39 (s, 1H, OH); 6.43 ppm (d, J=4.41 Hz, 1H); 6.13 ppm (t, J=1.7 Hz, J=8.17 Hz, 1H); 6.00 ppm (dd, J=3.6 and 5.07 Hz, 1H); 5.89 ppm (d, J=2.6 Hz, 1H); 5.74 ppm (dd, J=8.4 and 10.7 Hz, 2H); 3.7–3.3 ppm (s, br, NH$_3^+$); 2.54 ppm (s, 3H, CH$_3$). ESI-MS: 192 [M+1]$^+$(85).

| CHN analysis: | | | | | |
|---|---|---|---|---|---|
| (C$_{10}$H$_9$NOS.HCl) | % C | % H | % N | % Cl | % S |
| Calcd.: | 52.75 | 4.43 | 6.15 | 15.57 | 14.08 |
| Found: | 52.50 | 4.40 | 6.10 | 15.50 | 13.60 |

4. 3-Amino-2-(benzo[b]thiophen-2-yl)phenol hydrochloride

Boric acid derivative used: 1-benzothiophen-2-ylboric acid

Yield: 0.008 g (14% of the theoretical) MS (API-ES pos.): 242 [M+H]$^+$(50).

5. 3-Amino-2-(5-phenyl-2-thienyl)phenol hydrochloride

Boric acid derivative used: 5-phenyl-2-thienylboric acid

Yield: 0.048 g (16% of the theoretical) MS (API-ES neg.): 266 [M–H]$^-$ (100).

6. 3-Amino-2-(3,5-dimethylisoxazol-4-yl)phenol hydrochloride

Boric acid derivative used: 3,5-dimethyl-4-isoxazolylboric acid

Yield: 0.070 g (30% of the theoretical) MS (API-ES pos.): 227 [M+Na]$^+$ (100).

Examples 7 to 12

Hair Colorants

Hair colorant solutions of the following composition were prepared:

| | | |
|---|---|---|
| 1.25 mmol | of the substance of formula (I) as per Table 1 | |
| 1.25 mmol | of the developer as per Table 1 | |
| 10.0 g | of lauryl ether sulfate (28% aqueous solution) | |
| 9.0 g | of ammonia (22% aqueous solution) | |
| 7.8 g | of ethanol | |
| 0.3 g | of ascorbic acid | |
| 0.3 g | of disodium ethylenediaminetetraacetate hydrate | |
| to 100.0 g | water, demineralized | |

Just before use, 10 g of the above colorant solution was mixed with 10 g of a 6% aqueous hydrogen peroxide solution. The mixture was then applied to bleached hair. After an exposure time of 30 minutes at 40° C., the hair was rinsed with water, washed with a commercial shampoo and dried. Table 1 summarizes the resulting colorations.

TABLE 1

| | | | | Developer | | |
|---|---|---|---|---|---|---|
| Example No. | Coupler of Formula (I) | I 2,5-diamino-toluene sulfate | II 2,5-diamino-phenylethanol sulfate | III 4,5-diamino-1-(2'-hydroxy-ethyl)pyrazole sulfate | IV 4-aminophenol | V 2,4,5,6-tetra-aminopyrimidine sulfate |
| 7 | as per Example 1 | intense violet | intense violet | strawberry red | orange-brown | gray |
| 8 | as per Example 2 | violetish brown | violetish brown | strawberry red | weak orange | gray |
| 9 | as per Example 3 | dark-bluish violet | dark-bluish violet | strawberry red | bright pink | brown-green |
| 10 | as per Example 4 | light brown | — | pink | — | — |
| 11 | as per Example 5 | brown | brown | red | orange-brown | brown-gray |
| 12 | as per Example 6 | violetish gray | violetish gray | strawberry pink | weak orange | weak green |

Examples 13 to 24

Hair Colorants

Hair colorant solutions of the following composition were prepared:

| | |
|---|---|
| X g | of 3-aminophenol derivative of formula (I) (coupler K1 to K2 as per Table 4) |
| U g | of developer E8 to E15 as per Table 2 |
| Y g | of coupler K11 to K36 as per Table 4 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 30 g of the above colorant solution was mixed with 30 g of a 6% aqueous hydrogen peroxide solution. The mixture was then applied to bleached hair. After an exposure time of 30 minutes at 40° C., the hair was rinsed with water, washed with a commercial shampoo and dried. Tables 5 and 6 summarize the resulting colorations.

TABLE 2

| | Developers |
|---|---|
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E13 | N,N-bis-(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| | Direct Dyes |
|---|---|
| D2 | 6-chloro-2-ethylamino-4-nitrophenol |
| D3 | 2-amino-6-chloro-4-nitrophenol |

TABLE 4

| | Couplers |
|---|---|
| K1 | 3-amino-2-(3-thienyl)phenol |
| K2 | 3-amino-2-(2-thienyl)phenol |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene.HCl |
| K36 | 2-amino-5-methylphenol |

TABLE 5

Hair Colorants

| Dyes | Example No. 13 | 14 | 15 | 16 | 17 | 18 |
|---|---|---|---|---|---|---|
| | (Dye quantity in grams) | | | | | |
| K1 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

TABLE 6

Hair Colorants

| Dyes | Example No. 19 | 20 | 21 | 22 | 23 | 24 |
|---|---|---|---|---|---|---|
| | (Dye quantity in grams) | | | | | |
| K2 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

Examples 25 to 30

Hair Colorants

Hair colorant solutions of the following composition were prepared:

| | |
|---|---|
| X g | of 3-aminophenol derivative of formula (I) (coupler K1 as per Table 4) |
| U g | of developer E8 to E15 as per Table 2 |
| Y g | of coupler K11 to K36 as per Table 4 |
| Z g | of direct dye D2 and D3 as per Table 3 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 30 g of the above colorant solution was mixed with 30 g of a 6 % aqueous hydrogen peroxide solution. The mixture was then applied to hair. After an exposure time of 30 minutes at 40° C., the hair was rinsed with water, washed with a commercial shampoo and dried. Table 7 summarizes the resulting colorations.

TABLE 7

Hair Colorants

| | Example No. | | | | | |
|---|---|---|---|---|---|---|
| Dyes | 25 | 26 | 27 | 28 | 29 | 30 |
| | (Dye quantity in grams) | | | | | |
| K1 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K19 | 0.10 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

Unless otherwise indicated, all percentages given in the present patent application are by weight.

The invention claimed is:

1. An agent for coloring keratin fibers based on a developer-coupler combination, said agent containing, as the coupler, at least one 3-aminophenol derivative of formula (I), or a physiologically compatible salt thereof:

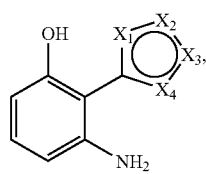

(I)

wherein $X_1$, $X_2$, $X_3$, and $X_4$, independently of each other, denote sulfur, nitrogen, N—R1, oxygen, C—R2, C—R3, C—R4, or C—R5, provided that at least one and at the most three of the $X_1$ to $X_4$ groups denote nitrogen, N—R1, sulfur, or oxygen and, if at least two heteroatoms are present in the formula (I), at the most one of the $X_1$ to $X_4$ groups denotes sulfur, N—R1, or oxygen;

R1 denotes hydrogen, a $(C_1$–$C_6)$-alkyl group, a phenyl group, a $(C_2$–$C_4$-hydroxy-alkyl group, or an acetyl group;

R2, R3, R4, and R5, independently of each other, denote hydrogen, a halogen atom, a cyano group, a $(C_1$–$C_4)$-alkyl group, a $(C_1$–$C_4)$-alkoxy group, a $(C_1$–$C_4)$-alkyl thioether group, a marcapto group, a nitro group, an amino group, a $(C_1$–$C_4)$-alkylamino group, a di$(C_1$–$C_4)$-alkylamino group, a hydroxy-$(C_2$–$C_4)$-alkyl-amino group, a di[hydroxy-$(C_2$–$C_4)$-alkyl]-amino group, a [dihydroxy-$(C_3$–$C_4)$-alkyl]amino group, a trifluoromethyl group, an acetyl group, a trifluoroacetyl group, a formyl group, a trimethylsilyl group, a $(C_1$–$C_4)$-hydroxyalkyl group, or a $(C_2$–$C_4)$-dihydroxyalkyl group; or two adjacent R2 to R5 groups together with a remaining part of the formula (I) form an annelated heterocyclic or carbocyclic, substituted or unsubstituted ring.

2. The agent as defined in claim 1, wherein said at least one 3-amino-phenol derivative of formula (I) is selected from the group consisting of 3-amino-2-(3-thienyl)-phenol, 3-amino-2-(3-furyl)-phenol, 3-amino-2-(pyrrol-3-yl)-phenol, 3-amino-2-(1-methyl-1H-pyrrol-3-yl)-phenol, 3-amino-2-(1,3-thiazol-2-yl)-phenol, 3-amino-2-(1,3-thiazol-5-yl)-phenol, 3-amino-2-(2-thienyl)-phenol, 3-amino-2-(2-furyl)-phenol, 3-amino-2-(pyrrol-2-yl)-phenol, 3-amino-2-(1-methyl-1H-pyrrol-2-yl)-phenol, 3-amino-2-(2-chloro-3-thienyl)-phenol, 3-amino-2-(2-methyl-3-thienyl)-phenol, 3-amino-2-(benzo[b]thiophen-2-yl)-phenol, 3-amino-2-(5-phenyl-2-thienyl)-phenol, 3-amino-2-(2-nitro-3-thienyl)-phenol, 3-amino-2-(2-amino-3-thienyl)-phenol, 3-amino-,2-(2-acetyl-3-thienyl)-phenol, 3-amino-2-(2-formyl-3-thienyl-yl)-phenol, 3-amino-2-(4-chloro-3-thienyl)-phenol, 3-amino-2-(4-methyl-3-thienyl)-phenol, 3-amino-2-(4-nitro-3-thienyl)-phenol, 3-amino-2-(4-amino-3-thienyl)-phenol, 3-amino-2-(4-acetyl-3-thienyl)-phenol, 3-amino-2-(4-formyl-3-thienyl)-phenol, 3-amino-2-(5-chloro-3-thienyl)-phenol, 3-amino-2-(5-methyl-3-thienyl)-phenol, 3-amino-2-(5-phenyl-3-thienyl]-phenol, 3-amino-2-(5-nitro-3-thienyl)-phenol, 3-amino-2-(5-acetyl-3-thienyl)-phenol, 3-amino-2-(5-amino-3-thienyl)-phenol, 3-amino-2-(5-formyl-3-thienyl)-phenol, 3-amino-2-(benzo[b]thiophen-3-yl)-phenol, 3-amino-2-(5-formyl-3-furyl)phenol, 3-amino-2-(3-chloro-2-thienyl)-phenol, 3-amino-2-(3-methyl-2-thienyl)-phenol, 3-amino-2-(3-nitro-2-thienyl)-phenol, 3-amino-2-(3-amino-2-thienyl)-phenol, 3-amino-2-(3-acetyl-2-thienyl)-phenol, 3-amino-2-(3-formyl-2-thienyl)-phenol, 3-amino-2-(4-chloro-2-thienyl)-phenol, 3-amino-2-(4-methyl-2-thienyl)-phenol, 3-amino-2-(4-nitro-2-thienyl)-phenol, 3-amino-2-(4-amino-2-thienyl)-phenol, 3-amino-2-(4-acetyl-2-thienyl)-phenol, 3-amino-2-(4-formyl-2-thienyl)-phenol, 3-amino-2-(5-chloro-2-thienyl-yl)-phenol, 3-amino-2-(5-methyl-2-thienyl)-phenol, 3-amino2-(5-nitro-2-thienyl)-phenol, 3-amino-2-(5-amino-2-thienyl)-phenol, 3-amino-2-(5-acetyl-2-thienyl)-phenol, 3-amino-2-(5-formyl-2-thienyl)-phenol, 3-amino-2-(5-formyl-2-furyl)-phenol, 3-amino-2-(5-nitro-1,3-thiazol-2-yl)-phenol, 3-amino-2-(5-amino-1,3-thiazol-2-yl)-phenol, 3-amino-2-(2-nitro-1,3-thiazol-5-yl)-phenol, 3-amino-2-(2-amino-1,3-thiazol-5-yl)-phenol, 3-amino-2-(3,5-dimethylisoxazol-4-yl)-phenol, 3-amino-2-(3,5-dimethyl-1H-pyrazol-4-yl)-phenol, and 3-amino-2-(5-nitro-4H-1,2,4-triazol-3-yl)-phenol.

3. The agent as defined in claim 1, wherein in formula (I): (i) $X_2$ denotes sulfur and $X_1$, $X_3$, and $X_4$ denote C—R2, C—R4, and C—R5, or (ii) $X_1$ denotes sulfur and $X_2$, $X_3$, and $X_4$ denote C—R3, C—R4, and C—R5.

4. The agent as defined in claim 1, wherein the at least one 3-aminophenol derivative of the formula (I) is selected from the group consisting of 3-amino-2-(3-thienyl)-phenol, 3-amino-2-(2-thienyl)-phenol, 3-amino-2-(benzo[b] thiophen-3-yl)-phenol, and 3-amino-2-(5phenyl-2thienyl)-phenol.

5. The agent as defined in claim 1, containing from 0.005 to 20 weight percent of said at least one 3-aminophenol derivative of the formula (I).

6. The agent as defined in claim 1, wherein the developer is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene 2-chloro-1,4-diamino-benzene, 1,4-diamino-2-(2-thienyl)-benzene, 1,4-diamino-2-(3-thienyl)-benzene, 1,4-diamino-2-(pyridin-3-yl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy) benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]-aniline, 4-[di(2-hydroxyethyl)amino]-aniline, 4-[di(2-hydroxyethyl)amino]-2methylaniline, 4-[(2-methoxyethyl)amino]-aniline, 4-[(3-hydroxypropyl)amino]-aniline, 4[(2,3-dihydroxypropyl)amino]-aniline, 1,4-diamino-2-(1-hydroxyethyl)-benzene, 1,4-diamino-2-(2-hydroxyethyl)-benzene, 1,4-diamino-2-(1-methylethyl)benzene, 1,3-bis-[(4-aminophenyl)-(2-hydroxyethyl)amino]-2-propanol, 1,4-bis-[(4aminophenyl)amino]butane, 1,8-bis-(2,5-diaminophenoxy)-3,6dioxaoctane, 4-aminophenol, 4-amino-3-methylphenol, 4-amino-3-(hydroxymethyl)-phenol, 4-amino-3-fluorophenol, 4-methylaminophenol, 4-amino-2-(aminomethyl)-phenol, 4-amino-2-(hydroxy-methyl)-phenol, 4-amino-2-fluorophenol, 4-amino-2-[(2-hydroxyethyl)amino]- methylphenol, 4-amino-2-methylphenol, 4-amino-2-(methoxymethyl)-phenol, 4-amino-2-(2hydroxyethyl)-phenol, 5-aminosalicylic acid, 2,5-diaminopyridine, 2,4,5,6-tetraamino-pyrimidine, 2,5,6-triamino-4-(1H)-pyrimidone, 4,5-diamino-1-(2-hydroxy-ethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methyl-phenol, and 1,2,4-trihydroxybenzene.

7. The agent as defined in claim 1, further comprising at least one additional coupler besides said at least one 3-amino-phenol derivative, and wherein said at least one additional coupler is selected from the group consisting of N-(3-dimethylaminophenyl)urea; 2,6-diaminopyridine; 2-amino-4-[(2-hydroxy-ethyl)amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5methylbenzene; 2 4-di[(2-hydroxyethyl)-amino]-1,5-dimethoxybenzene; 2,3-diamino-6-methoxypyridine; 3-amino-6-methoxy-2-(methylamino) pyridine; 2,6-diamino-3,5-dimethoxypyridine; 3,5-diamino-2,6-dimethoxypyridine, 1,3-diaminobenzene; 2,4-diamino-1-(2-hydroxyethoxy)benzene; 1,3-amino-4-(2, 3-dihydroxypropoxy)-benzene; 1,3-diamino-4-(3-hydroxypropoxy)benzene; 1,3-diamino-4-(2methoxyethoxy)-benzene; 2,4-diamino-1,5-di(2-hydroxyethoxy)benzene; 1-(2-aminoethoxy)-2,4-diaminobenzene; 2-amino-1-(2hydroxyethoxy)-4-methylaminobenzene; 2,4-diaminophenoxyacetic acid; 3-[di(2-hydroxyethyl)amino]-aniline; 4-amino-2-di[(2-hydroxyethyl)amino]-1-ethoxybenzene; 5-methyl-2-(1-methylethyl)-phenol; 3-[(2-hydroxyethyl)amino]-aniline; 3-[(2-aminoethyl)amino]-aniline; 1,3-di-(2,4-diaminophenoxy)-propane; di(2,4-diaminophenoxy)methane; 1,3-diamino-2,4-dimethoxybenzene; 2,6-bis-(2-hydroxyethyl)amino-toluene; 4-hydroxyindole, 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichloro-phenol; 3-amino-2-methylphenol; 3-amino-2-chloro-6-methylphenol; 3-amino-phenol; 2-[(3-hydroxy-phenyl)amino]-acetamide; 5-[(2-hydroxyethyl)amino]-4-methoxy-2-methylphenol; 5-[(2-hydroxyethyl)amino]-2-methylphenol; 3-[(2-hydroxyethyl)amino]-phenol; 3-[(2methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxy-pyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxy-naphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1, 3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2-hydroxyethyl)-amino]-1, 3-benzodioxole; 6-bromo-1-hydroxy-3,4-methylenedioxybenzene; 3,4-diaminobenzoic acid; 3,4-dihydro-6-hydroxyl-1,4(2H)benzoxazine; 6-amino-3,4-dihydro-1,4(2H) benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole; and 2,3-indolinedione.

8. The agent as defined in claim 1, containing from 0.005 to 20 weight percent of the developer and containing from 0.005 to 20 weight percent of the coupler, based on a total amount of the agent.

9. The agent as defined in claim 1, further comprising at least one direct dye compound.

10. The agent as defined in claim 1, and having a pH from 6.5 to 11.5.

11. The agent as defined in claim 1, consisting of a hair colorant.

12. The ready-for-apply agent for oxidative dyeing of keratin fibers which, in a medium appropriate for dyeing, contains at least one developer compound, at least one coupler compound and at feast one oxidant, wherein said at least one coupler compounds comprises at least one 3-aminophenol derivative of formula (I), or a physiologically compatible salt thereof:

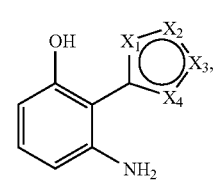

(I)

wherein $X_1$, $X_2$, $X_3$, and $X_4$, independently of each other, denote sulfur, nitrogen, N—R1, oxygen, C—R2, C—R3, C—R4, or C—R5, provided that at least one and at the most three of the $X_1$ to $X_4$ groups denote nitrogen, N—R1 sulfur, or oxygen and, if at least two heteroatoms are present in the formula (I), at the most one of the $X_1$ to $X_4$ groups denotes sulfur, N—R1, or oxygen;

R1 denotes hydrogen, a $(C_1–C_6)$-alkyl group, a phenyl group, a $(C_2–C_4)$-hydroxy-alkyl group, or an acetyl group;

R2, R3, R4, and R5, independently of each other, denote hydrogen, a halogen atom, a cyano group, a $(C_1–C_6)$-alkyl group, a $(C_1–C_4)$-alkoxy group, a $(C_1–C_4)$-alkyl thioether group, a mercapto group, a nitro group, an amino group, a $(C_1–C_4)$-alkylamino group, a di$(C_1–C_4)$-alkylamino group, a hydroxy-$(C_2–C_4)$-alkyl-amino group, a di[hydroxy-$(C_2C_4)$-alkyl]-amino group, a [dihydroxy-$(C_3–C_4)$-alkyl]amino group, a trifluoromethyl group, an acetyl group, a trifluoroacetyl group, a formyl group, a trimethylsilyl group, a $(C_1–C_4)$-hydroxyalkyl group, or a $(C_2–C_4)$-dihydroxy-alkyl group; or two adjacent R2 to R5 groups together with a remaining part of the formula (I) form an annelated heterocyclic or carbocyclic, substituted or unsubstituted ring.

13. A method for oxidative dyeing of hair, particularly human hair, said method comprising the steps of:

a) prior to application to the hair, mixing a hair colorant with an oxidant to form a ready-to-apply hair coloring mixture;

b) applying the hair coloring mixture to the hair and allowing the hair coloring mixture to act on the hair at a temperature from 15 to 50° C. for 10 to 45 minutes; and then c) rinsing the hair with water, optionally washing the hair with a shampoo and then drying the hair;

wherein said hair colorant comprises at least one 3-aminophenol derivative of formula (I), or a physiologically compatible salt thereof:

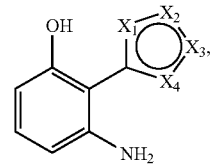

(I)

wherein $X_1$, $X_2$, $X_3$, and $_4$, independently of each other, denote sulfur, nitrogen, N—R1 oxygen, C—R2, C—R3, C—R4, or C—R5, provided that at least one and at the most three of the $X_1$ to $X_4$ groups denote nitrogen, N—R1, sulfur, or oxygen and, if at least two heteroatoms are present in the formula (I), at the most one of the $X_1$ to $X_4$ groups denotes sulfur, N—R1, or oxygen;

R1 denotes hydrogen, a $(C_1–C_6)$-alkyl group, a phenyl group, a $(C_1–C_4)$-hydroxy-alkyl group, or an acetyl group;

R2, R3, R4, and R5, independently of each other, denote hydrogen, a halogen atom, a cyano group, a $(C1–C_6)$-alkyl group, a $(C_1–C_4)$-alkoxy group, a $(C_1–C_4)$-alkyl thioether group, a mercapto group, a nitro group, an amino group, a $(C_1–C_4)$-alkylamino group, a di$(C_1–C_4)$-alkylamino group, a hydroxy-$(C_2–C_4)$-alkyl-amino group) a di[hydroxy-$(C_2–C_4)$-alkyl]-amino group, a [dihydroxy-$(C_3–C_4)$-alkyl]amino group, a trifluoromethyl group, an acetyl group, a trifluoroacetyl group, a formyl group, a trimethylsilyl group, a $(C_1–C_4)$-hydroxyalkyl group, or a $(C_2–C_4)$-dihydroxyalkyl group; or two adjacent R2 to R5 groups together with a remaining part of the formula (I) form an annelated heterocyclic or carbocyclic, substituted or unsubstituted ring.

\* \* \* \* \*